United States Patent [19]

Steuer et al.

[11] Patent Number: 4,711,248

[45] Date of Patent: Dec. 8, 1987

[54] PHYSIOLOGICAL PRESSURE MONITOR

[75] Inventors: Robert R. Steuer, Salt Lake City, Utah; David H. Harris, Boise, Id.

[73] Assignee: Biokinetics, Inc., Salt Lake City, Utah

[21] Appl. No.: 556,912

[22] Filed: Dec. 1, 1983

[51] Int. Cl.[4] .......................... A61B 5/00; A61B 5/04

[52] U.S. Cl. .................................... 128/748; 128/733; 128/741

[58] Field of Search ............................... 128/670–671, 128/688–690, 706, 709–710, 731–733, 748, 715, 672–673, 675

[56] References Cited

U.S. PATENT DOCUMENTS

| Re. 30,966 | 6/1982 | Hargens et al. | 128/748 |
|---|---|---|---|
| 3,662,743 | 5/1972 | Amarante et al. | 128/748 |
| 4,073,287 | 2/1978 | Bradley et al. | 128/642 |
| 4,108,166 | 8/1978 | Schmid | 128/710 X |
| 4,129,125 | 12/1978 | Lester et al. | 128/671 |
| 4,191,196 | 3/1980 | Bradley et al. | 128/733 |
| 4,270,547 | 6/1981 | Steffen et al. | 128/736 X |
| 4,291,705 | 9/1981 | Severinghaus et al. | 128/733 |
| 4,312,361 | 1/1982 | Nicholson et al. | 128/748 |
| 4,344,441 | 8/1982 | Radke | 128/733 |
| 4,347,851 | 9/1982 | Jundanian | 128/673 X |
| 4,407,295 | 10/1983 | Steuer et al. | 128/671 X |
| 4,447,230 | 5/1984 | Gula et al. | 604/126 X |
| 4,448,203 | 5/1984 | Williamson et al. | 128/733 |

FOREIGN PATENT DOCUMENTS

| 57-03166 | 9/1982 | Japan | 128/733 |
|---|---|---|---|
| 7711798 | 5/1979 | Netherlands | 128/748 |

OTHER PUBLICATIONS

Nicholson et al., "A Measurement System for Monitoring Brain Retraction Pressure"; Conference: IEEE 1979, Frontiers of Engr. in Health, pp. 193-195.

"Cuffed Endotracheal Tubes: Mucosal Pressures and Tracheal Wall Blood Flow" by Philip Dobrin, MD, PhD, Thomas Canfield, MS, *The American Journal of Surgery*, pp. 562-568, vol. 133, May 1977.

"Acute Compartment Syndromes: Diagnosis and Treatment with the Aid of the Wick Catheter" by Scott et al., *The Journal of Bone and Joint Surgery*, pp. 1091-1095, Dec. 1978.

"The Endotracheal Cuff: A Comparative Study" by Dobrin, Ph.D., et al., *Anesthesia and Analgesia . . . Current Researches*, pp. 456-460, vol. 53, No. 3, May-Jun. 1974.

"Transtracheal Pressure Exerted by Endotracheal Tube Cuffs" by Doyle & Dobrin, *J. Biomechanics*, 1975, vol. 8, pp. 247-252.

"Compartmental Syndrome: An Unified Concept" by Matsen, III, M.D., *Clinical Orthopaedics & Related Research*, No. 113, pp. 8-13, Nov.-Dec. 1975.

"Compartment Syndromes of the Leg" by Mubarak, MD & Hargens, PhD, *The Western Journal of Medicine*, pp. 429-430, Nov. 1980.

"The Wick Catheter Technique for Measurement of Intramuscular Pressure" by Mubarak et al., *The Journal of Bone and Joint Surgery*, pp. 1016-1020.

Matsen, F. A. et al., "A Model Compartmental Syndrome in Man with Particular Reference to the Quantification of Nerve Function," *The Journal of Bone and Joint Surgery*, vol. 59-A, No. 5, Jul. 1977, pp. 648-653.

Scholander, P. F., "Negative Pressure in the Interstitial Fluid of Animals," *Science*, vol. 161, No. 3839, Jul. 26, 1968, pp. 321-328.

Rorabeck, C. H., "Compartment Syndrome after Tibial Fracture," *Orthopaedic Consultation*, vol. 5, No. 4, Apr. 1984, pp. 1-7.

*Primary Examiner*—Henry J. Recla
*Assistant Examiner*—Angela D. Sykes
*Attorney, Agent, or Firm*—Mason, Fenwick & Lawrence

[57] ABSTRACT

A portable physiological pressure monitoring device adapted for being attached to a body part of a patient in which the compartment pressure is to be continuously monitored. The device includes an alarm for indicating when a predetermined maximum pressure limit is exceeded or when a predetermined minimum pressure is not maintained for a certain period of time. The pressure device also includes a hydrophobic filter which separates a catheter and the sensing components of the pressure device for providing sterile operation. A warning also sounds when a battery falls below a given voltage level. Finally, the pressure monitoring device also includes apparatus for measuring nerve conduction velocity and action potential to facilitate better diagnosis and monitoring of compartment syndrome.

7 Claims, 8 Drawing Figures

PHYSIOLOGICAL PRESSURE MONITOR

BACKGROUND OF THE INVENTION

1. Field of the Invention

The present invention relates to a portable pressure monitor with a disposable cathether, in general, and to a universal physiologic pressure monitor finding particular application in the monitoring of compartment syndrome, in particular.

2. Background of the Prior Art

A compartment syndrome results from increased tissue pressure in a closed fascial space or compartment of the human body. A detailed overview of compartmental syndrome is presented in an article entitled, "Compartmental Syndrome: a Unified Concept," by Dr. Frederick A. Matsen, III, *Clinical Orthopaedics and Related Research*, Number 113, November-December, 1975, pages 9–13. This increased tissue pressure can adversely affect the circulation to the nerves and muscles within the involved compartment, ultimately leading to the death of those tissues. Tibial fractures and severe contusions are the most common causes of compartment syndrome. Besides these, there are a great number of additional problems which can cause the syndrome. Among these are drug overdose with limb compression, third degree burns, arterial occlusion with post-ischemic swelling. Finally, vigorous exercise can also contribute to compartment syndrome.

In the initial stages of compartment syndrome, the primary injury causes hemorrhage, edema, or both, in the closed fascial compartment of the extremities of the person who has been injured. The natural course of an untreated compartment syndrome may be devastating and can result in muscle contracture and neural deficiency known as Volkmann contracture. Some additional names given to some of the conditions in which compartmental syndrome plays a central role are as follows: Volkmann's ischemia; Compartment syndrome; Impending ischemic contracture; Rhabdomyolysis; Crush syndrome; Exercise ischemia; Local ischemia; Traumatic tension ischemia in muscles; Acute ischemic infarction; Ischemic necrosis; Anterior tibial syndrome; Peroneal nerve palsy; Calf hypertension; amd Phlegmasia cerulea dolens.

Thus, the control of pressure build-up within a muscular compartment in order to prevent nerve and muscle damage is recognized in the prior art and certain prior art techniques employing a Sorensen wick catheter in conjunction with manometer are known. However, these techniques are quite time consuming. Further, the bulky size of known pressure monitors prevents their use in all areas of a hospital.

In measuring the pressure within a fascial space, under the prior art technique, a Sorensen wick catheter is inserted within the fascial space and the other end of the catheter is secured to a large pressure monitor that includes a manometer. The wick catheter technique was developed in 1968 for measurement of subcutaneous pressure. In this regard, see "The Wick Catheter Technique for Measurement of Intramuscular Pressure" by Dr. S. J. Mubarak et al, *The Journal of Bone and Joint Surgery*, Vol. 58-A, No. 7, October 1976, pp. 1016–1020. Also see "A Model Compartmental Syndrome in Man with Particular Reference to the Quantification of Nerve Function," by Dr. Frederick A. Matsen, III, et al, *The Journal of Bone and Joint Surgery*, Vol. 59-A, No. 5, July 1977, pp. 648–653. The pressure generated within the fascial space is directly proportional to the mass of the fluid within the manometer multiplied by the gravitational constant and further multiplied by the height difference between the location of the fascial space and the location of the pressure transducer associated with the pressure monitor. Therefore, relative height changes between the location of the wick catheter and the pressure transducer can create a hydrostatic pressure head which effects the readout accuracy of the pressure monitor. For this reason, such monitors must possess complex zeroing circuitry in order to insure that when there is a height difference between the location of the fascial space being monitored and the pressure transducer there is full compensation for the developed hydrostatic pressure.

Thus, there is a need for a portable, low-cost pressure monitor which can easily monitor the pressure build-up within a muscle compartment and, when a dangerous condition exists within the compartment, to notify medical personnel of the condition. The present invention is directed toward filling that need.

SUMMARY OF THE INVENTION

The present invention basically comprises a portable housing for enclosing circuitry for monitoring and sensing pressure through a catheter connected to a compartment of a patient being monitored. A hydrophobic filter is interposed at the point of connection between the catheter and pressure transducer enclosed in the portable housing. Because of its size, shape, and contour, the housing is adapted to be attached to the patient in close proximity to the fascial space or muscular compartment being monitored so that the wick catheter within the muscle compartment and the pressure transducer are maintained in the same relative vertical elevation, thus eliminating any problems associated with hydrostatic pressure differential. The monitoring device also includes an indicator for providing a digital readout of the pressure in millimeters (mm) of mercury or centimeters (cm) of water. Further, should a maximum pressure be exceeded, provision is made in the pressure monitor for both audio and visual alarms. Likewise, when a given minimum pressure is not maintained for a given period of time, an alarm also sounds. The pressure monitor also includes a low battery indicator along with an alarm for indicating when power supply is inadequate.

Also forming part of the present invention is circuitry employed to generate a stimulating pulse of current which is applied to tissue within the muscle compartment being monitored. This stimulating pulse is supplied by way of a pair of stimulating electrodes to the skin over the muscle compartment. An array of three pick-up electrodes is connected to the skin near the affected muscles and, through these electrodes, an EMG (electromyograph) signal is developed. The pick-up electrodes are typically located ahead of (distally) the stimulating electrodes. The EMG output is sent through an optoisolating circuit to protect the patient from unwanted shock and, through a series of circuit devices, finally resulting in a display of the amplitude of the action potential sensed by the pick-up electrodes. The EMG output is also processed through an electronic counting circuit to provide a display of the nerve conduction velocity on an additional LCD display provided within the housing of the pressure monitor.

In view of the foregoing, it is a primary objective of the present invention to provide a portable, highlyaccurate and reliable, electronic physiological pressure monitor suitable for continuous monitoring and indication of dangerous levels of compartmental pressures within a patient.

It is another objective of the present invention to provide a physiological pressure monitor that is not susceptable to variation in sensed pressure due to relative vertical displacement of the monitor and the compartment being sensed.

It is a further objective of the present invention to provide a physiological pressure monitor wherein the use thereof is greatly facilitated by less skilled operators.

It is a still further objective of the present invention to provide a physiological pressure monitor which, during continuous monitoring, produces an alarm when the compartmental pressure exceeds a predetermined limit.

These and further objects, advantages and features of the present invention will be more readily apparent upon review of the succeeding disclosure taken in connection with the accompanying drawings. The invention, however, is pointed out with particularity by the appended claims.

DETAILED DESCRIPTION OF THE INVENTION

Figures 1, 2:
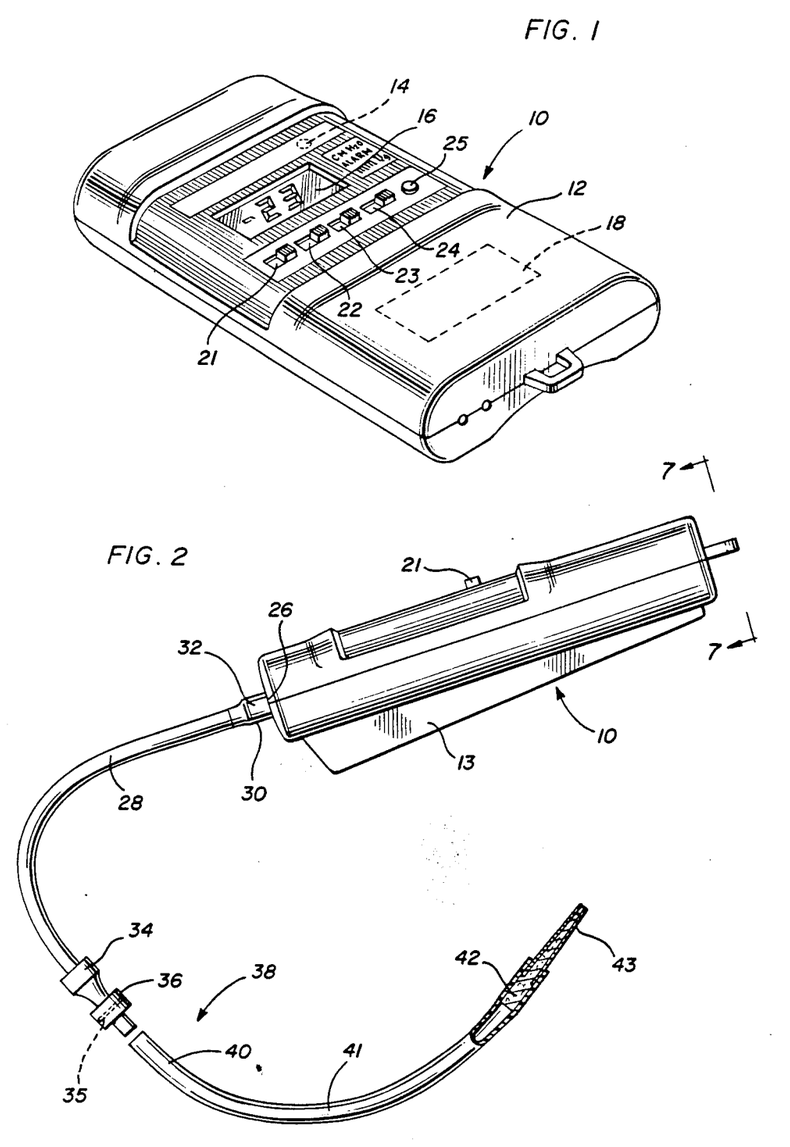
FIG. 1 is a perspective view showing the front panel of the housing for an embodiment of the pressure monitor.
FIG. 2 is a plan view partly in schematic showing the operation of the pressure monitor of FIG. 1 in conjunction with a wick catheter for measurement of pressure within a muscle compartment.

With reference to FIGS. 1 and 2, the housing associated with a preferred embodiment of the pressure monitor is generally designated as 10. With specific reference to FIG. 1, the front panel 12 of the pressure monitor 10 is generally shown. In the upper right hand corner of the front panel is an aperture 14. Under the aperture is a piezoelectric beeper which is used to produce an audible alarm. How and under what circumstances the alarm is produced will be described in greater detail hereinafter.

Also provided on the face plate or frontal panel are two displays 16 and 18 (shown in phantom). Display 16, which is preferably an LCD (liquid crystal diode) display, is used to provide a readout of muscle compartment pressure in either millimeters of mercury or centimeters of water. The display can also provide a visual readout of the amplitude of the action potential associated with the muscle within the fascial space being monitored. LCD display 18, on the other hand, provides a readout of the nerve conduction velocity associated with the same muscles. In another preferred embodiment, multiplexing may be employed so that one display 16 can display all readings and display 18 may be eliminated.

Four switches 21 through 24 are provided on the front panel. Switch 21 is a single pole, single throw switch used to turn the unit on and off. Switch 22 is a double pole, double throw switch with a central off position. Switch 22 is used to set the parameters under which the audible alarm will be activated. Switch 23 is used to determine whether the display of the pressure readout on LCD display 16 will be in centimeters of water or millimeters of mercury. Finally, switch 24 is used to set whether the display 16 will show the action potential of stimulated muscle or the pressure within the muscle compartment being monitored.

With reference now to FIG. 2, the side of the pressure monitor of FIG. 1 is generally shown. At the back of the device is an aperture 26 to which is secured a flexible tubing 28. One end 30 of the tubing is secured to a mating fixture 32 provided at aperture 26. The other end of tubing 28 terminates in a luer lock 34. A hydrophobic filter 36 such as those made by Gelman Sciences, Ann Arbor, Mich., has one end connected to the luer lock. The other end of the filter is connected to a wick catheter or probe 38. The wick catheter consists of a flexible tubing 40 terminating at its distal end in a wick 42. The wick and catheter are implanted within the muscular compartment in which pressure is to be monitored.

Figure 3:
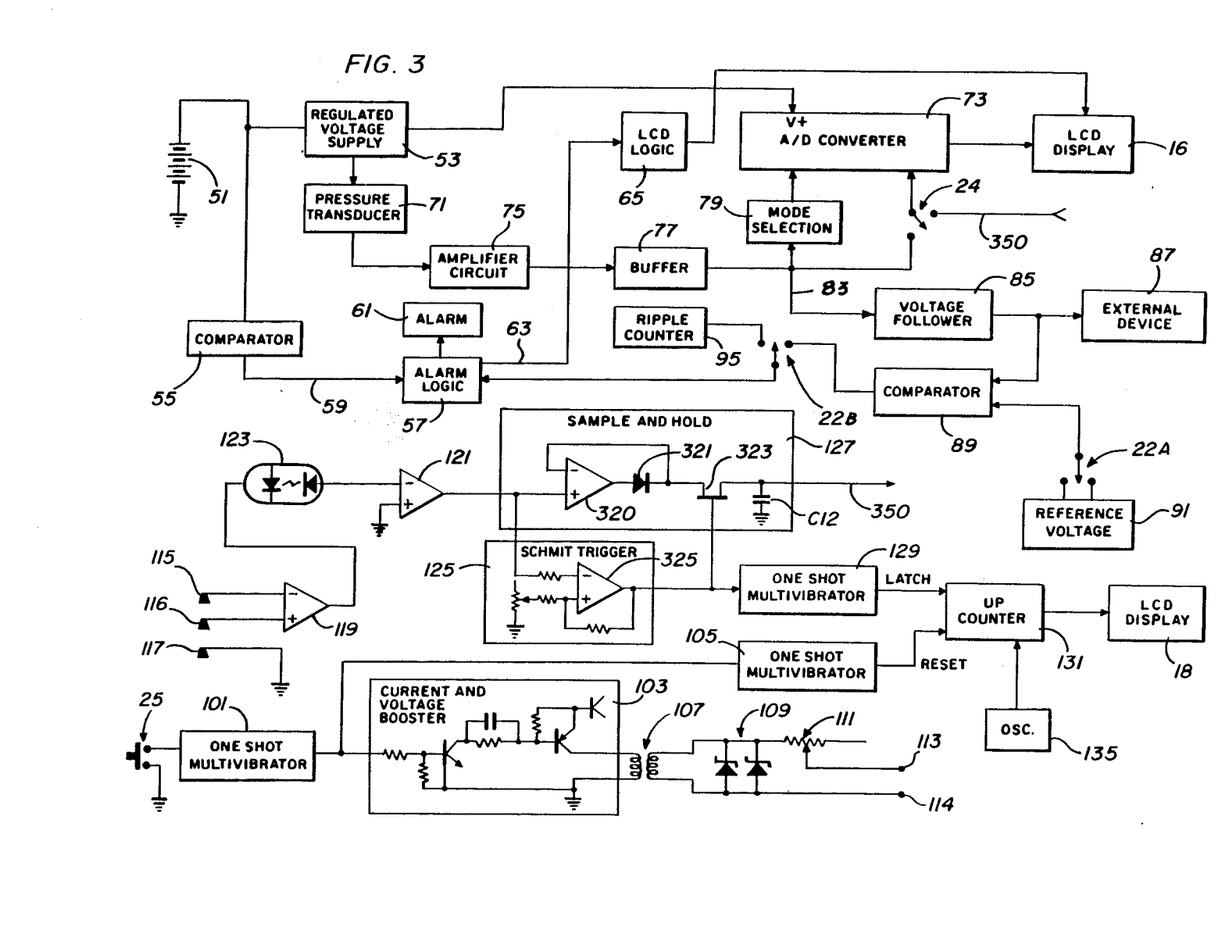
FIG. 3 is a block diagram showing the electronic circuitry found in a preferred embodiment of the subject invention.

FIG. 3 shows a block diagram of an embodiment of a pressure monitor embodying the teaching of the present invention. A battery 51 is connected to a regulated voltage supply 53. The battery is also connected to a comparator 55 which is used to generate a low battery signal that is fed into alarm logic 57 via lines 59. Alarm logic 57 has an output connected to an audible alarm 61. The alarm logic 57 contains a further output 63 which is connected to LCD logic 65. In turn, the LCD logic is connected to the LCD display 16. The LCD logic 65 causes the display to operate in a manner to be described hereinafter.

The regulated voltage supply 53 which produces a constant 5 volt output is connected to the pressure transducer 71 and to an A-to-D converter 73. One such A-to-D converter bears production designation No. 1CL7106 and is manufactured by Intersil, of Sunnyvale, Calif. The output from the pressure transducer is fed through an amplifier circuit 75, the output of which is passed through a buffer 77. The buffer acts to prevent loading of the transducer through negative feedback. The output of the buffer is then fed through a mode selection circuit 79, the output of which is fed to the A-to-D converter 73 in order to cause certain operations to be carried out within the A-to-D converter.

The output of the buffer 77 is also fed through a switch 24 which in one mode feeds the signal developed at the buffer 77 directly into the input of the A-to-D converter. At the same time, the output from the buffer is fed on lines 83 to a voltage follower 85. The output of the voltage follower may be used to drive an external device 87 in a manner to be described in detail hereinafter.

The output of the voltage follower is also fed to a comparator 89 which also receives one of two reference voltages developed by a reference voltage circuit 91. The output of the comparator is fed to one of the pair of poles of switch 22. Closure of switch 22 directs the output of the comparator to the alarm logic 57. When the switch 22 is in its alternative position, the output of a ripple counter 95 is directed to the alarm logic.

Switch 25 completes a circuit in order to activate a one shot multivibrator 101. The output of this vibrator is sent to a current and voltage booster 103 and also to a further one shot multivibrator 105. The output of the current and voltage booster 103 is fed through the low end of a step-up transformer 107. The other side of the transformer is connected to a parallel arrangement of two zener diodes 109 and then to a current limiting variable resistor 111. The current limiting resistor and the other lead introduce the stepped up voltage and current to a pair of stimulating electrodes 113 and 114.

Three pick-up electrodes 115 through 117 are used to measure the amplitude of the action potential developed in muscle. Electrode 117 is connected to ground. Electrodes 115 and 116 provide the input to an high impedance operational amplifier 119. One such amplifier bears product designation No. LM363 and is made by National Semiconductor. The output of amplifier 119 is coupled to an A/C gain amplifier 121 through a conventional optoisolator 123 consisting of a phototransistor and an infrared emitter. The output of the amplifier 121 is fed to a Schmitt trigger 125 and to a sample-and-hold 127. The output of the Schmitt trigger is also fed to a one shot multivibrator 129. The output of multivibrator 129 is used to latch an up-counter 131. The output of multivibrator 105 is used to reset the up-counter. An oscillator 135 clocks the up-counter 131. The output of the up-counter provides a readout of the nerve conduction velocity on LCD display 18 of the muscle found in the compartment being monitored.

The output of the sample-and-hold is fed to the switch 24 which controls the introduction of either the output of the sample-and-hold or the output of the buffer 77 as an information signal into the A-to-D converter 73.

Figure 4A:
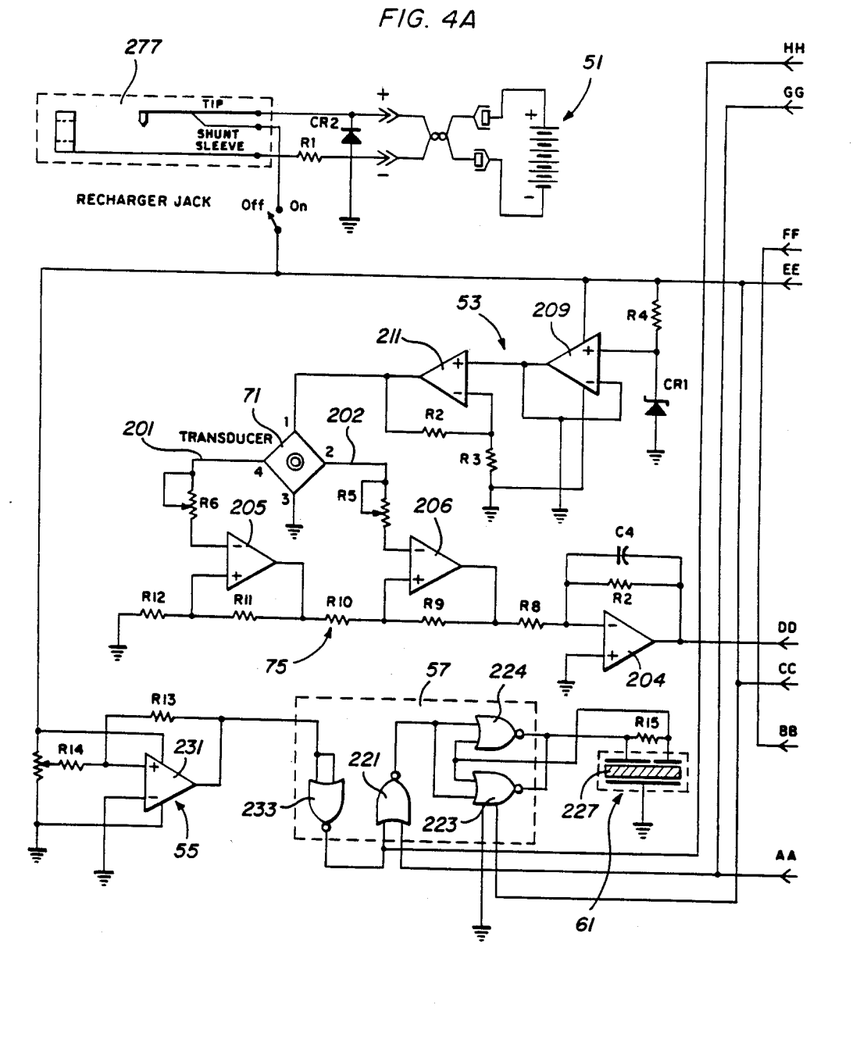
FIGS. 4a and 4b are detailed schematic diagrams showing an implementation of the pressure detecting circuitry of FIG. 3.
Figure 4B:
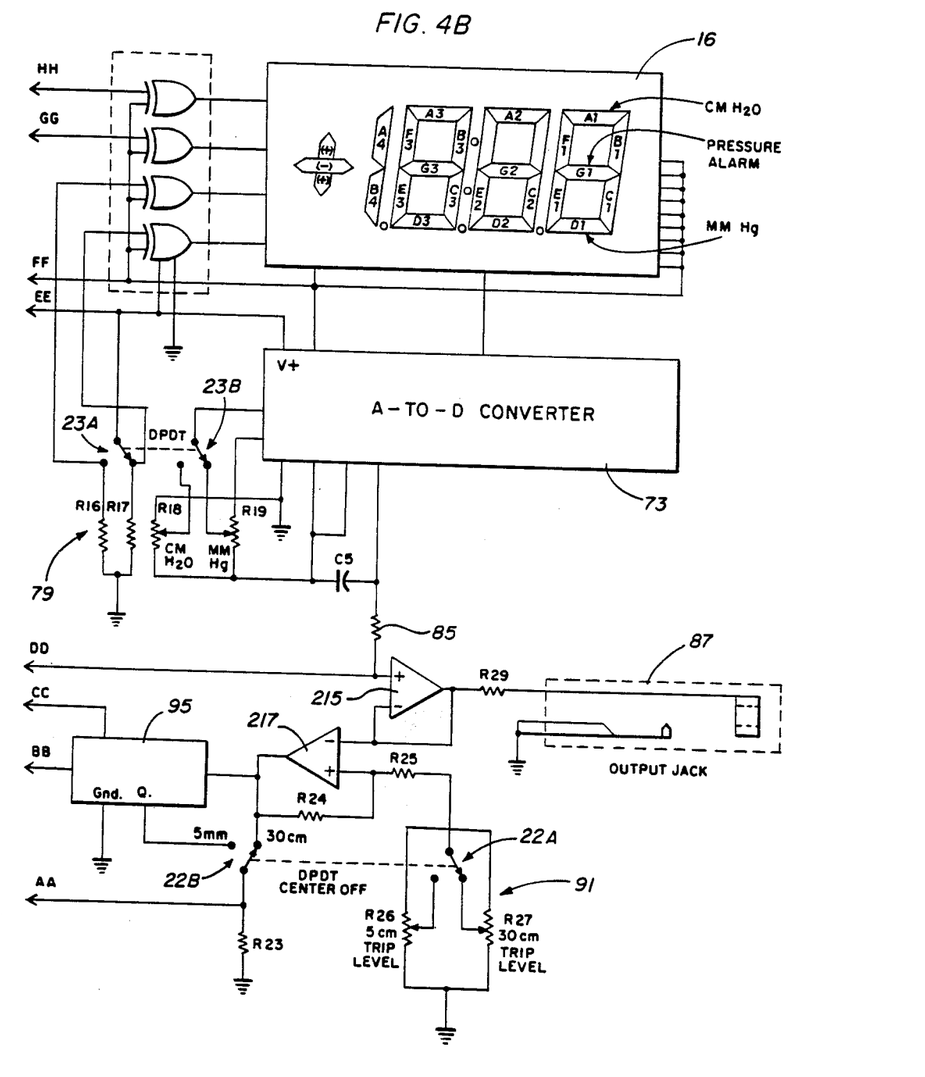

Having described generally the elements which constitute the electronic circuitry associated with the pressure monitor, a detailed description of the operation of the circuitry will be provided with reference to FIG. 4.

Operation of the pressure monitor 10 centers around the pressure transducer 71 which in a preferred embodiment is a quad-bridge formed with four piezoresistive elements which respond to changes in pressure by producing impedance changes. Within pressure transducer 71, changes in impedance produce outputs on lines 201 and 202 as a differential voltage proportional to applied pressure. To compensate for manufacturing variations in transducers and their associated circuitry, potentiometers R5 and R6 are placed in lines 201 and 202, respectively. The small voltages developed across these added potentiometers correct null and offset voltages through the entire pressure signal path and allow the display 16 to read precisely zero when there is zero pressure.

Signals from the transducer 71 are amplified with a standard instrumentation amplifier arrangement 75 using operational amplifiers (op-amps) 205 and 206 and resistors R8 through R12. Two other operational amplifiers serve to provide stable operating voltages for the system. Op-amp 209, within the regulated voltage supply 53, buffers the output of the reference diode CR1 and develops the common voltage of 2.5 volts. A non-inverting arrangement of op-amp 211 provides a gain of exactly 2. Thus, the output of op-amp 211 provides the desired +5 volts used to power the pressure transducer 71.

The output of the instrumentation amplifier 75 is processed through an op-amp 204 forming part of buffer 77. Capacitor C4 in buffer 77 provides feedback for op-amp 204 to compensate for noise injected into the pressure signal from the piezoelectric alarm 61. This output of the buffer 77 feeds the A-to-D converter 73 via one pair of poles of switch 24. Op-amp 215 is part of voltage follower 85 which buffers the pressure signal to both drive an external device 87 such as a strip chart recorder, oscilliscope, etc. and to drive op-amp 217 that is part of voltage comparator 89. Pole pair 22A of switch 22 determines which reference voltage from reference voltage block 91 is compared with the pressure signal. Pole pair 22B of switch 22 selects where the output of comparator 89 is sent. In the mode where it is desired to have an alarm sound upon the detection of 30 mm of mercury or greater, variable resistor R27 sets the trip level and the ouput of comparator 89 drives one input of NOR gate 221. In another mode of operation, to be described in detail hereinafter, the pressure monitor may be used as a ventilator disconnect monitor. In this case, it is important to have the trip level set at 5 mm of mercury. To accomplish this, variable resistor R26 sets the trip level; the output of comparator 89, however, does not drive NOR gate 221 directly. Instead, the NOR gate is driven by the Q output of ripple counter 95. When switch 22 selects the 30 mm mode, pressures of 30 mm of mercury or greater cause the alarm to sound. Pressures under 5 mm of mercury in the 5 mm mode release the reset line of ripple counter 95 and allow it to count up, clocked by the backplane oscillator located within the A-to-D convertor 73. When the Q output becomes true, approximately 16 seconds later, NOR gate 221 is activated and the alarm 61 sounds.

The audio alarm 61 is driven in parallel by NOR gates 223 and 224. Resistor R15 is connected from the output of piezoelectric crystal 227 to an input of each of these gates. Resistor R15 in the configuration forces NOR gates 223 and 224 into a linear mode of operation. The small amount of feedback from the piezoelectric crystal 227 of the alarm 61 is adequate to form an oscillator at a resonant frequency of the crystal. The second input of each NOR gate 223 and 224 serves as a control to the oscillator. When the output of NOR gate 221 is low (0 volts), the oscillator operates, and visa versa. The other input to NOR gate 221 is generated by comparator 55. It compares a signal derived from the battery voltage through resistors R14 and R28 to the 2.5 volt reference. Correctly setting resistor R28 causes the output of op-amp 231, forming part of comparator 55, to go to zero when the battery voltage is low. NOR gate 233 inverts the signal and provides the proper logic levels to drive NOR gate 221. Thus, either a pressure alarm condition or a low battery condition or both will trigger the alarm 61. The output of NOR gate 233 also drives an exclusive or (XOR) gate 241 to turn on the "LO BAT" indicator on the LCD display 16. XOR gate 241 and three other XOR gates 243, 245 and 247 constitute the LCD logic. The output of pole pair 22B of switch 22 also drives an XOR gate 243, illuminating segment 371 of the rightmost digit on the LCD display 16 to indicate the presence of a pressure alarm. It should be noted that if no pressure alarms are desired, switch 22 can be placed in its center-off position. Resistor R23 will keep the pressure alarm input line of NOR gate 221 from ever being asserted.

Two other XOR gates 245 and 247 drive segments 373 and 375 to indicate which scale (mm of mercury or cm of water) is selected on the display 16. One pole pair 23A of double pole, double throw switch 23, which forms part of mode selection 79, enables or disables the correct LCD segment while resistors R16 and R17, also forming part of mode selection 79, ensure that the LCD segment not selected stays off. The other pole pair 23B of switch 23 selects from two reference voltages on potentiometers R18 and R19. The reference voltage from variable resistor R18 relates to display of cm of water, whereas the reference voltage from resistor R19 relates to display of mm of mercury. Suitable adjustments of these potentiometers provides correct scaling of the digital display to read in the proper units. All other segments of the LCD display 16 are driven directly from the A-to-D converter itself. Segments which are not used are tied to the backplane within the A-to-D convertor.

A-to-D converter 73 is configured to provide three samples per second of the input voltage. All the circuitry is powered from a 9 volt rechargeable battery. Rectifier CR2 safeguards against battery mispolarity, and resistor R1 safely limits the charger current when recharging. Note that when recharging through jack 277, power to the pressure monitor circuitry is disabled. The unit will not operate while connected to an A/C recharging system.

FIG. 2 schematically shows a conventional catheter assembly 38 for use with the compartment pressure device just described. The catheter 40, having an absorbent wick 42 exhibiting a wicking action and terminating in a needle 43, is inserted into the muscle compartment of the patient being monitored. Through the channel of the needle 43, the pressure of the compartment is conveyed through the chamber 41 of the catheter. The catheter 40 couples a hydrophobic filter 36 which in turn couples the pressure sensing transducer 71 through tube 28. Housing 10 encloses the circuitry of FIG. 3. The hydrophobic filter 36 includes a membrane 35 which provides isolation between the muscle compartment and the sensing circuitry of the device. The barrier 35 shields the compartment from viruses and bacteria.

Figure 5:
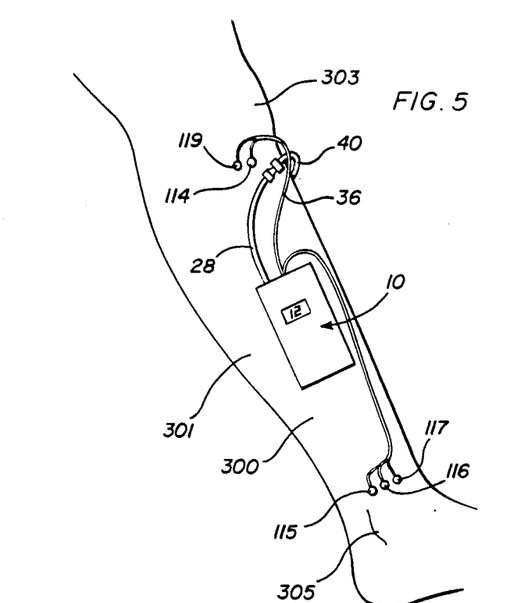
FIG. 5 is a schematic diagram showing the placement of the pressure monitor on the leg of a patient.
Figure 6:
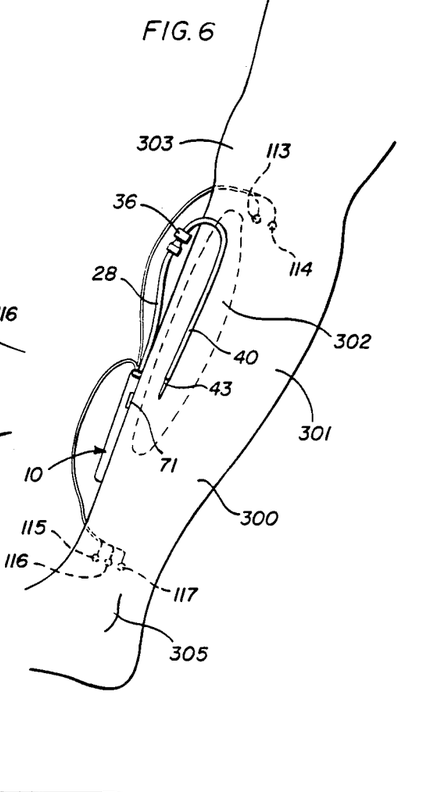
FIG. 6 is a schematic diagram showing the relative placement of both pressure monitor and an implanted wick catheter.
Figure 7:
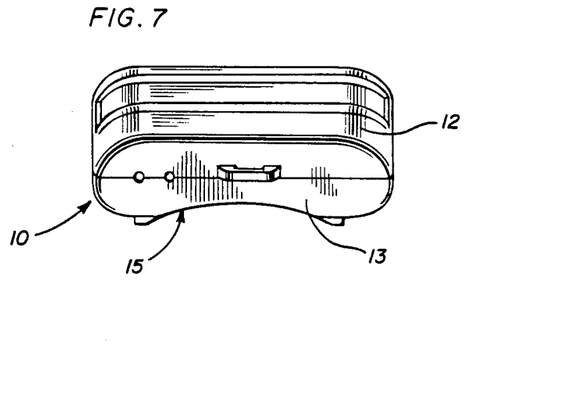
FIG. 7 is a view taken along lines 7—7 of FIG. 2.

FIGS. 5 and 6 show in schematic form an exemplary attachment of the pressure monitor 10 mounted to the leg 300 of a patient. As seen, the housing 10 is fixedly attached in proximity to the muscle compartment 302 being monitored. FIG. 7 shows a front end view of housing 10. As can be seen, the underside 13 of housing 10 has an elongated trough 15 configured generally to accommodate a leg or arm of the patient. The catheter 40 and the pressure transducer 71 are fixed in approximately the same relative vertical elevation, and therefore, do not require zeroing as the patient moves about since the compartment and the pressure monitoring device move together.

Also forming part of the pressure monitor is a circuit employed to generate a stimulating pulse of current which is applied above the affected muscle compartment. This stimulating pulse, which is normally 200 microseconds long, and 80 volts in amplitude, is applied by way of stimulating electrodes 113 and 114 to the skin over the affected muscle compartment. Separate from the stimulating electrodes are three pick-up electrodes 115 through 117 which sense an EMG output. As shown in FIGS. 5 and 6, for typical monitoring of a calf muscle 301, the stimulating electrodes 113, 114 are positioned near knee 303, whereas the pick-up electrodes 115 through 117 are positioned distally near ankle 305. The EMG signal passes through a high impedance instrumentation amplifier 119 and then is coupled to the main circuit through an optoisolator 123. Human skin tissue generally exhibits high impedance and, therefore, the instrumentation amplifier also exhibits high impedance to allow the signal from the skin to get through. The optoisolator is used to prevent a high current shock to the patient. The EMG signal then passes through an A/C gain amplifier 121 which acts as a band pass filter. The sample-and-hold 127 generally comprises an operational amplifier 320 arranged in series with a diode 321. There is feedback from the output of the op-amp 320 back to the negative input and this configuration produces an ideal diode arrangement. The diode is then connected to an N channel MOS device 323 which acts as a switch. A capacitor C12 accumulates charge and performs the hold function of the sample-and-hold device. An operational amplifier 325 is configured as a Schmitt trigger 125. The output of the Schmitt trigger is used to open and close the MOS device 323 and thus perform the sample function. The output of the Schmitt trigger also causes the multivibrator 129 to latch the up-counter 131. The charge across the capacitor C12 is an analog voltage which is fed to the A-to-D convertor and displayed on LCD display 16. The quantity displayed is the amplitude of the action potential.

When it is desired to use the stimulation mode, the push button 25 is activated to close the circuit and activate the one shot multivibrator 101. The output of the multivibrator passes through one shot multivibrator 105 to reset the up-counter and at the same time passes through a current and voltage booster to provide a 9 volt input to the step-up transformer 107. The pair of parallel zener diodes 109 protects the patient from a high voltage input. At the same time, the current limiting resistor 111 limits the amount of current delivered to the patient through the stimulating electrodes 113 and 114.

The output of the up-counter is fed to the LCD display 18. This output is representative of the nerve conduction velocity. The time interval from the occurrence of the stimulating pulse as initiated by pressing switch 25 to the time that the EMG action potential occurs is counted up on the up-counter 131 and displayed on the LCD display 18 as nerve conduction velocity.

By monitoring three major parameters, the condition of the muscle bundle and the nerve fibers within that muscle bundle can be physiologically determined immediately. The three major parameters include: (1) the pressure inside the muscle bundle, (2) the amplitude of the action potential, and (3) the nerve conduction velocity through the affected muscle bundle. All three of these parameters give the clinician an immediate real time, and continuous readout of the status of the nerves and the muscle compartment affected by the trauma.

The output from the voltage follower 85 provides a simple way to interface with existing EKG and oscilliscope type recorders in intensive care units, anesthesia units, postanesthetic recovery units, and other similar areas. The clinician can now look at action potential (contours), nerve conduction time, and actual pressure wave form deviations in a simple and easy manner.

As can be appreciated from the foregoing discussion, a preferred embodiment of the pressure monitor 10 is used to monitor compartment syndrome. However, it can readily be appreciated that the pressure monitor may be used for any purpose where it is desired to provide an immediate display and monitoring pressure. Among possible uses of the pressure monitor are to measure and monitor endotracheal cuff pressure, central venous pressure, airway pressure, carpel-tunnel syndrome pressure, intracranial pressure, uterine pressure contraction, and extremity tourniquet pressure. All of the above conditions may be monitored by the small, portable hand-held device which has readouts in centimeters of water or millimeters of mercury on the digital LCD display 16. The pressure monitor of the subject invention allows for continuous monitoring of physiologic pressures over time. The pressure monitor of the subject invention can readily be employed for these other functions by connecting the conventional catheters currently used to measure the pressure within the particular part of the body to the appropriate connection 32 provided at the back of the pressure monitor housing 10.

Even with these possible uses, the pressure monitor performs a primary function in presenting an easy to use, portable pressure monitor with specific interest to alarm at 30 mm of mercury or above. The portable, low pressure range monitor is configured so that it may be attached to the limb in which the wick 42 catheter has been inserted. Because of its size, the pressure monitor may be secured at the exact same level as the place where the catheter 40 is inside the muscle compartment. This is particularly important, since any height difference between the pressure transducer 71 as contained in the pressure monitor and the cite where the muscle compartment is located within the limb, falsifies the pressure reading. As is well known, pressure is directly proportional to the mass of a column of fluid times the gravitational constant times height. Therefore, any difference in height changes hydrostatic pressure to affect readout accuracy. By instructing the user to mount the pressure monitor at the same point where the wick catheter has been inserted into the muscle compartment, even paramedical or nontechnical people can use the pressure monitor accurately.

Another important factor is the hydrophobic filter 35 in line with the catheter. Since the transducer 71 is non-sterile, the patient's sterility is maintained with the hydrophobic filter, providing an antiviral, antibacterial barrier to the passage of sterile fluid, or even fluid contact across the hydrophobic member. This disposable member in line, accurately transmits pressure from one side of the membrane to the other, yet maintains sterility without the need to sterilize each pressure transducer.

Pressure transducers in the past, and today, have certain inherent problems regarding their stability. Many of the pressure transducers suffer from temperature instability. In addition, an offset voltage difference from transducer to transducer is seen as a user tries to "zero" and "re-zero" the integrated pressure transducer while it is being used. The present invention provides electronic circuitry which accomplishes, in a straight forward manner, a millivolt per psi transfer function to a direct digital readout in millimeters of mercury or centimeters of water without the need for temperature compensating circuitry over the range of about 25° C.±20° C. In addition, the present invention provides for a transducer offset voltage that remains ratio metrically stable during the use of the transducer. This circuitry provides for a reference voltage, which is used in the transducer offset circuitry and also becomes the reference voltage to the A-to-D convertor. Hence, resistor selection and matching to the transducer becomes much less critical and easier to do on a mass production basis.

The decision to have an alarm sound at 30 mm of mercury is important. As has been determined in laboratory animals and humans, neuromuscular function begins to be impaired when the compartmental pressure exceeds 30 mm of mercury. Therefore, when the alarm occurs in the pressure monitor, the physician then decompresses (usually by fascitomy) the involved compartment of muscle and nerves, thereby saving these tissues.

The Schmitt trigger 217 in comparator 89 helps to set the 30 mm level for triggering the alarm and also provides the proper amount of hysteresis necessary to insure stable clinical use, since minor fluctuations in pressure can occur transiently. It has been determined that in order to give stable, accurate clinical results, a 30 mm of mercury alarm has approximately 5 millivolts of hysteresis. The low battery alarm has approximately 20 millivolts of hysteresis and the disconnect alarm has approximately 2.5 millivolts of hysteresis. The amount of hysteresis (electronic memory) decreases the number of nuisance alarms due to "minor" fluctuations of pressure or voltage.

In certain situations, it may be desirable to use the pressure monitor as a ventilator disconnect alarm. In this particular situation, the catheter would be inserted into the endotracheal tube connected to the ventilator. The other end of the catheter would be connected to the pressure monitor. A 5 mm of mercury "trip" point is also provided through switch 22. As the ventilator is being used, pressure changes occur in the endotracheal tube. If there is not a 5 mm pressure change within the endotracheal tube, a 16 second delay is enabled during which time if 5 mm of pressure still do not occur in the breathing circuit of the ventilator, then an alarm will sound, indicating to the clinician that there has been a disconnection of the ventilator from the patient. This particular alarm is critical to prevent serious damage to the patient. In particular, because the catheter 40 is in the endotracheal tube, the pressure monitor immediately alarms the clinician that either the ventilator has been disconnected, shut off, or some other catastrophic event has occurred. In this way, the clinician is alerted that air must be immediately given to the patient.

From the above teachings, it is seen that many other changes, modifications and adaptations to the compartmental pressure device may be made by those skilled in the art. Accordingly, it is not the intent of the inventor to limit the scope of his invention to what is exactly shown and described, but instead, the invention is limited only by the appended claims.

We claim:

1. A physiological pressure device for continuously monitoring a muscle compartment of a patient, said device comprising:

a portable housing including means for attaching said housing in proximity to a muscle bundle associated with the muscle compartment of the patient being monitored;

an elongated implantable catheter having one end terminating in a probe exhibiting wicking action, said probe adapted to be implanted within the muscle compartment of the patient;

pressure sensing means disposed in said portable housing means and connected to the other end of said catheter means for sensing pressure in said muscle compartment by way of said implanted probe;

means within said housing and responsive to said pressure sensing signal for providing a first information signal indicative of the pressure inside said muscle compartment;

stimulating means including electrode means mounted on the skin of the patient adjacent said muscle compartment for controllable delivering a shock to the exterior skin in the vicinity of the muscle compartment being monitored;

pick-up means contacting the exterior skin adjacent the muscle compartment of the patient for sensing the action potential developed when said stimulating means is delivering a shock;

means within said housing and responsive to the output of said pick-up means for providing a second information signal indicative of the amplitude of the action potential of said muscle bundle;

means within said housing and responsive to said second information signal for providing a third information signal indicative to the nerve conduction velocity through said muscle bundle;

display means for displaying said information signals in eye-readable form; and means for selectively passing said information signals to said display means.

2. A physiological pressure device as recited in claim 1 wherein said display means comprises an alarm which warns of the attainment in said compartment of a predetermined pressure limit.

3. A physiological pressure device as recited in claim 2 wherein said alarm is on-off switchable.

4. A physiological pressure device as recited in claim 1 wherein said display means comprises a visual display which indicates pressure and an audio alarm which warns of the attainment in said compartment of a predetermined pressure limit.

5. A physiological pressure device as recited in claim 4 wherein said alarm is on-off switchable.

6. A physiological pressure device as recited in claim 1 further comprising hydrophobic filter means interposed between said catheter and said sensing means for isolating said sensing means from said compartment.

7. A physiological pressure device as recited in claim 1 wherein said housing further includes battery means for supplying power to said pressure sensing means and means for indicating a low battery condition when the voltage supplied by said battery means falls below a given level.

* * * * *